(12) United States Patent
Shimizu et al.

(10) Patent No.: US 7,450,742 B2
(45) Date of Patent: Nov. 11, 2008

(54) INFORMATION PROCESSING APPARATUS, INFORMATION PROCESSING SYSTEM, INFORMATION PROCESSING METHOD, STORAGE MEDIUM, AND PROGRAM

(75) Inventors: Satoshi Shimizu, Kanagawa (JP); Shinya Tanaka, Tokyo (JP); Tsukasa Sako, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 1004 days.

(21) Appl. No.: 10/969,790

(22) Filed: Oct. 20, 2004

(65) Prior Publication Data

US 2005/0086720 A1    Apr. 21, 2005

Related U.S. Application Data

(63) Continuation of application No. PCT/JP03/05660, filed on May 6, 2003.

(30) Foreign Application Priority Data

May 8, 2002   (JP)   ............... 2002-132808
Jun. 11, 2002  (JP)   ............... 2002-170372

(51) Int. Cl.
*G06K 9/00* (2006.01)
*H05G 1/10* (2006.01)
*G06F 17/30* (2006.01)

(52) U.S. Cl. .................. 382/128; 378/101; 726/27
(58) Field of Classification Search ............ 382/128, 382/129, 130, 131, 132, 133, 134; 378/46, 378/63, 90, 92, 98.4, 98.6, 98.9, 101, 140; 702/8, 40, 172; 706/27
See application file for complete search history.

(56) References Cited

U.S. PATENT DOCUMENTS 7,006,678 B2 *  2/2006  Sawada ............... 382/132

FOREIGN PATENT DOCUMENTS

| EP | 0 855 659 A1 | 7/1998 |
| EP | 1 026 603 A2 | 8/2000 |
| JP | 2000-41957 A | 2/2000 |
| JP | 2001-154984 A | 6/2001 |
| JP | 2001-217827 A | 8/2001 |
| JP | 2001-273365 A | 10/2001 |

(Continued)

OTHER PUBLICATIONS

Supplementary European Search Report of EP Application No. 03723239.4—Date of Completion of Search: Mar. 15, 2006—3 pages.

(Continued)

*Primary Examiner*—Abolfazl Tabatabai
(74) *Attorney, Agent, or Firm*—Morgan & Finnegan, LLP

(57) ABSTRACT

In an information processing apparatus which transfers target information to an external data processing device to process the information, and saves the processed information, a data management unit stores second identification information corresponding to the target information in association with the target information to which first identification information is attached. The first changing unit deletes the first identification information from the target information and adds the corresponding second identification information to the target information in the data management unit. The transfer unit transfers the target information processed by the first changing unit to the external data processing device.

21 Claims, 11 Drawing Sheets

FOREIGN PATENT DOCUMENTS

| | | |
|---|---|---|
| JP | 2001-309158 A | 11/2001 |
| JP | 2002-055919 A | 2/2002 |
| JP | 2002-189953 A | 7/2002 |
| WO | WO 01/08077 A1 | 2/2001 |
| WO | WO 02/19222 A1 | 3/2002 |

OTHER PUBLICATIONS

International Searching Authority; Japanese Patent Office; "PCT International Search Report"; corresponding to International Application No. PCT/JP03/05660; date of mailing Aug. 12, 2003; (7 pages).

* cited by examiner

FIG. 6

EXAMINATION NUMBER = 011213001

DIAGNOSIS REQUEST FORM

REQUEST DATA

HOSPITAL NAME : ○○ HOSPITAL
HOSPITAL CODE : 123456
DOCTOR IN CHARGE : TARO YAMAMOTO
DIAGNOSIS PURPOSE : MEDICAL CHECK
DIAGNOSIS REPORT DEADLINE :
DECEMBER 20, 2001

PATIENT DATA

PATIENT NUMBER : 1234567890
PERSONAL INFORMATION
NAME : ICHIRO SUZUKI
ADDRESS : CHUO-KU TOKYO
TELEPHONE : ○○○-○○○
DIAGNOSIS INFORMATION
SEX : MALE
DATE OF BIRTH : JANUARY 1, 1962
WEIGHT : 60 kg
BLOOD PRESSURE : 140 mmHg
BLOOD GLUCOSE LEVEL : 126 mg/dl
MEDICAL HISTORY : DIABETES

IMAGE DATA

IMAGE NUMBER : 1000456
PHOTOGRAPHING APPARATUS : XX-X
PHOTOGRAPHY DATE AND TIME :
2001 12 13 09 : 20
LEFT/RIGHT EYE : LEFT

IMAGE NUMBER : 1000457
PHOTOGRAPHING APPARATUS : XX-X
PHOTOGRAPHY DATE AND TIME :
2001 12 13 09 : 22
LEFT/RIGHT EYE : RIGHT

401 — SELECT/SET DIAGNOSING DOCTOR
402 — REQUEST DIAGNOSIS

FIG. 7

DIAGNOSING DOCTOR SELECTION SETTING

DIAGNOSING DOCTOR LIST

| PRIORITY | NAME OF DOCTOR | SPECIALTY | TITLE | SCHEDULE 14 15 16 17 18 19 20 |
|---|---|---|---|---|
| 1 | HANAKO ISHIKAWA | DIABETES | INSTRUCTOR | O O O O O X X |
| 2 | KAZU MATSUMOTO | DIABETES | INSTRUCTOR | X X O O O O O |
| 3 | KENICHI HORI | HYPERPIESIA | ASSISTANT PROFESSOR | O O X X O X X |
| 4 | HIROSHI ITO | DIABETES | PROFESSOR | X X X O O O X |

ADD DOCTOR    DELETE DOCTOR    CHANGE PRIORITY LEVEL

APPLY    CANCEL

FIG. 8

DIAGNOSIS REQUEST LIST

XX HOSPITAL OPHTHALMOLOGY DEPARTMENT ▶

| EXAMINATION NUMBER | REQUESTED DOCTOR NAME | EXAMINATION PURPOSE | REPORT DEADLINE | STATE |
|---|---|---|---|---|
| A12-2323123 | YAMAMOTO | MEDICAL CHECK | 2001.12.20 | WAIT FOR DIAGNOSIS |
| A12-2323124 | YAMAMOTO | MEDICAL CHECK | 2001.12.20 | WAIT FOR DIAGNOSIS |
| A12-2323125 | YAMAMOTO | MEDICAL CHECK | 2001.12.20 | WAIT FOR DIAGNOSIS |
| D31-0011223 | TANAKA | MEDICAL CHECK | 2001.12.20 | WAIT FOR DIAGNOSIS |
| D31-0011224 | TANAKA | DETAILED EXAMINATION | 2001.12.18 | DIAGNOSED/WAIT FOR CONFIRMATION |
| D21-0011225 | TANAKA | DETAILED EXAMINATION | 2001.12.18 | DIAGNOSED/WAIT FOR CONFIRMATION |
| K31-9898777 | SUZUKI | DETAILED EXAMINATION | 2001.12.18 | |
| K31-9898778 | SUZUKI | MEDICAL CHECK | 2001.12.18 | WAIT FOR DIAGNOSIS |

DISPLAY

FIG. 10

EXAMINATION NUMBER = 011213001
EXAMINATION NUMBER = A12-2323123

DIAGNOSIS REPORT CONFIRMATION    STATE: WAIT FOR DIAGNOSIS

REQUEST DATA
HOSPITAL NAME : ○○ HOSPITAL
HOSPITAL CODE : 123456
DOCTOR IN CHARGE : TARO YAMAMOTO
DIAGNOSIS PURPOSE : MEDICAL CHECK
DIAGNOSIS REPORT DEADLINE : DECEMBER 20, 2001

PATIENT DATA
PATIENT NUMBER : NONDISCLOSURE
PERSONAL INFORMATION
NAME : ICHIRO SUZUKI
ADDRESS : CHUO-KU TOKYO
TELEPHONE : ○○-○○○○
DIAGNOSIS INFORMATION
SEX : MALE
DATE OF BIRTH : JANUARY 1, 1962
WEIGHT : 60 KG
BLOOD PRESSURE : 140 mmHG
BLOOD GLUCOSE LEVEL : 126 mg/dl
MEDICAL HISTORY : DIABETES

IMAGE DATA

IMAGE NUMBER : 1000456
PHOTOGRAPHING APPARATUS
: XX-X
PHOTOGRAPHY DATE AND TIME
: 2001 12 13 09:20
LEFT/RIGHT EYE : LEFT

IMAGE NUMBER : 1000457
PHOTOGRAPHING APPARATUS
: XX-X
PHOTOGRAPHY DATE AND TIME
: 2001 12 13 09:22
LEFT/RIGHT EYE : RIGHT

DIAGNOSIS RESULT ENTRY FIELD
HANAKO ISHIKAWA
NAME OF DISEASE : NONE
COMMENT ON FINDINGS : NO ABNORMAL FINDINGS IN LEFT AND RIGHT EYES

REQUEST RE-EXAMINATION

CONFIRM REQUEST SOURCE

INFORMATION PROCESSING APPARATUS, INFORMATION PROCESSING SYSTEM, INFORMATION PROCESSING METHOD, STORAGE MEDIUM, AND PROGRAM

This is continuation of International Application Serial No. PCT/JP03/05660, filed May 6. 2003 in English and is herein incorporated by reference.

TECHNICAL FIELD

The present invention relates to an information processing apparatus, an information processing system, an information processing method, a computer-readable storage medium storing a program for executing the method, and the program which are used for an apparatus or system for processing medical information (e.g., image data obtained by X-ray imaging and the like) in the medical field.

BACKGROUND ART

Conventionally, imaging diagnosis in the medical field indicates that image information obtained by X-ray imaging is output onto an X-ray film, and a doctor or the like observes (interprets) the film image through a radiograph viewer.

In pursuit of ease of observing a region to be diagnosed, a general X-ray film is set to have a contrast corresponding to the density range of 1.0 to about 1.5 D in which the film image can be easily observed. For this reason, if imaging conditions slightly differ from desired conditions, overexposure or underexposure occurs, resulting in imposing adverse effects on imaging diagnosis by image interpretation.

Assume, in particular, that when an object to be imaged (patient or the like) is imaged by X-rays, X-ray imaging is performed for each of a plurality of regions (regions to be diagnosed) constituting the object (divisional imaging). In such a case, since the respective portions to be diagnosed on X-ray films differ in contrast and diagnosis purpose, various attempts are being made to obtain images suitable for imaging diagnosis.

With the recent advances in computers, computers have proliferated into the medical field. This trend has rapidly accelerated in the field of imaging diagnosis as well; there has been an astonishing proliferation of various types of CTs, ultrasound diagnostic equipment, diagnostic equipment using radio isotopes, and the like.

Under the circumstances, there has been developed the concept "comprehensive imaging diagnosis" in which, for example, various types of diagnosing devices are connected through computers to comprehensively diagnose various types of modality images.

Images on X-ray films are essentially analog images, which are used most frequently in imaging diagnosis and regarded important. In spite of this, however, these images have not been fit to the above comprehensive imaging diagnosis and have caused a bottleneck in computerization in the field of imaging diagnosis.

Recently, X-ray imaging apparatuses using solid-stage image sensing devices have been developed, and images (X-ray images) obtained by X-ray imaging have begun to be processed as digital data by using computers. Such techniques allow contrast adjustment of X-ray images that have already been obtained by X-ray imaging and re-imaging due to failure in X-ray imaging.

As X-ray images are digitalized, X-ray images with stabler image quality can be saved, and various kinds of image processing can be done on the basis of the digital data of such X-ray images.

For example, image processing such as temporal difference processing can be performed, in which an X-ray image obtained by preceding X-ray imaging and an X-ray image obtained by current X-ray imaging are digitally positioned to each other, and the difference is obtained. This operation is effective in terms of imaging diagnosis.

Furthermore, with the proliferation of the Internet, various kinds of data processing can be done on the Internet, and the symptom of the development of service type businesses has emerged.

For example, the above temporal difference processing function can be served on the Internet. In addition, for example, medical information (various kinds of medical information including X-ray images) in an intranet can be served on the Internet.

In the above conventional data processing method for the expansion of services on the Internet and the like, the following problems arise.

For example, when medical information and the like inside an intranet (information inside the intranet will also be referred to as "intranet information" hereinafter) are to be served on the Internet, sending intranet information onto the Internet poses a problem in terms of external leakage. For this reason, when a service on the Internet is to be used, external leakage of intranet information must be minimized.

In addition, when a service is provided on the Internet, some medical facilities other than authentic users may illicitly use the service. Authentication of service users may prevent this. However, as the external transmission of intranet information is restricted, it becomes more difficult to authenticate senders.

DISCLOSURE OF INVENTION

Accordingly, the present invention has been made to solve the above problems, and has as its object to provide an information processing apparatus, information processing system, and information processing method which can reliably prevent information leakage and reliably protect information, and a computer-readable storage medium storing a program for executing this operation, and the program.

More specifically, information leakage from the information saving side is prevented, and identification of information between the information saving side and the information processing side is inhibited. In addition, the information processing side is prevented from receiving information other than predetermined information.

According to the present invention, the foregoing object is attained providing an information processing apparatus which externally transfers target information to process the information, and saves the processed information, comprising:

storage means for storing second identification information corresponding to the target information in association with the target information to which first identification information is attached;

first changing means for deleting the first identification information and adding the corresponding second identification information to the target information in the storage means;

transfer means for externally transferring the target information processed by the first changing means; and saving means for saving the target information processed at an external transfer destination to which the information is transferred by the transfer means.

According to the present invention, the foregoing object is attained providing an information processing apparatus which is connected, through a network, to a requesting terminal which generates diagnosis request data and a diagnosing terminal which input diagnosis result data with respect to the diagnosis request data, comprising:

first reception means for receiving, through the network, diagnosis request data to which a specific examination number is attached from the requesting terminal;

conversion means for converting the examination number attached to the diagnosis request data into an examination request number;

first transmission means for transmitting, to the diagnosing terminal through the network, the diagnosis request data to which the examination request number is attached;

second reception means for receiving the diagnosis result data with respect to the diagnosis request data from the diagnosing terminal through the network; and second transmission means for inversely converting the examination request number attached to the diagnosis result data into the examination number and transmitting the diagnosis result data to the requesting terminal through the network.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 6 is a view for explaining a diagnosis request form window according to the second embodiment of the present invention;

FIG. 7 is a view for explaining a diagnosing doctor selection setting window according to the second embodiment of the present invention;

FIG. 8 is a view for explaining a diagnosis request list window according to the second embodiment of the present invention;

FIG. 10 is a view for explaining a diagnosis report confirmation window according to the second embodiment of the present invention.

BEST MODE FOR CARRYING OUT THE INVENTION

The embodiments of the present invention will be described below with reference to the accompanying drawings.

FIRST EMBODIMENT

Figure 1:
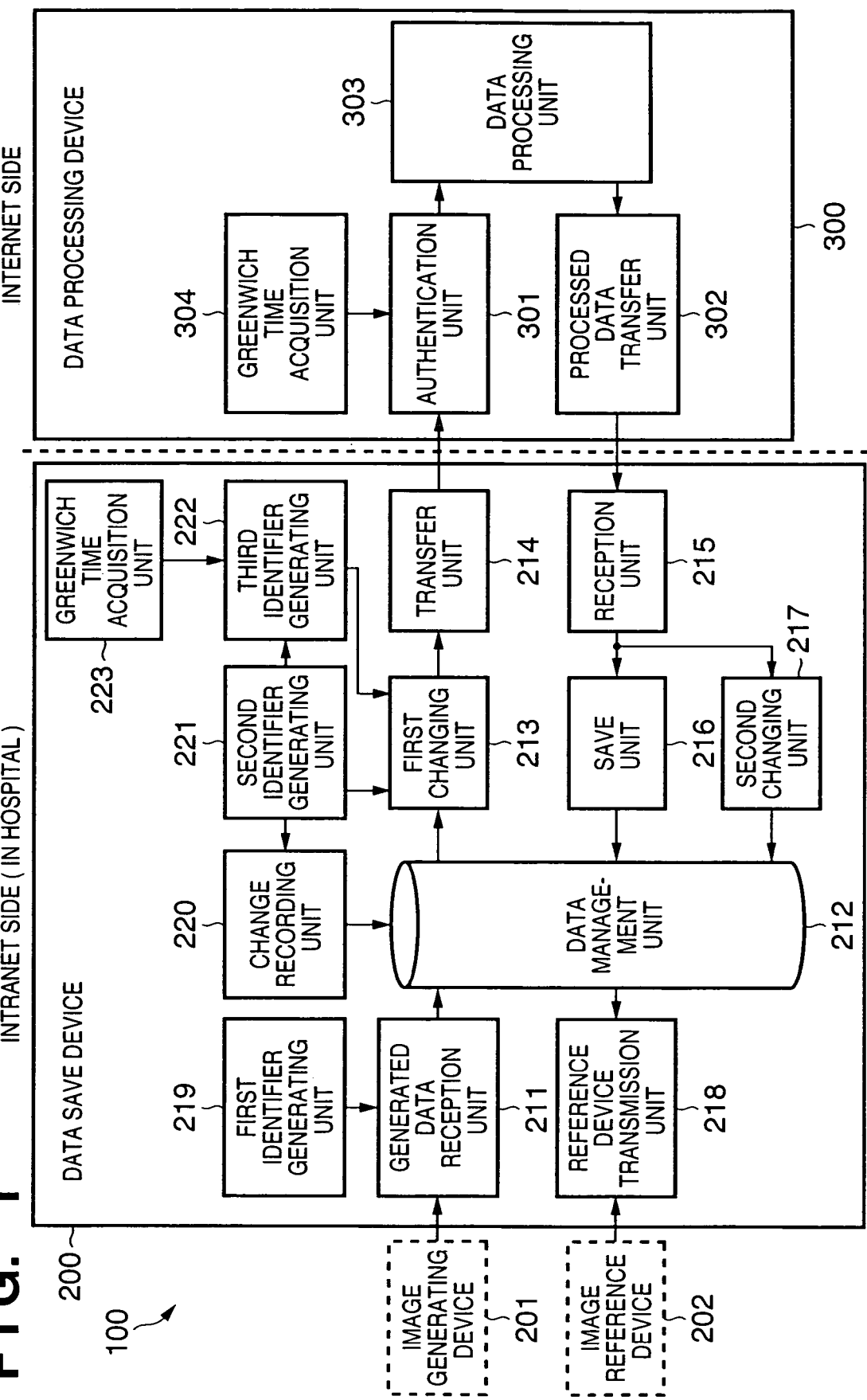
FIG. 1 is a block diagram showing the arrangement of a data save processing system according to the first embodiment of the present invention.

The present invention is applied to a data save processing system 100 like the one shown in FIG. 1.

The data save processing system 100 according to the first embodiment is configured to prevent leakage of information from a data save device 200, inhibit data identification between the data save device 200 and a data processing device 300, and inhibit the data processing deice 300 from receiving data other than predetermined data.

In brief, for example, in a data processing device which sends out data (target data including image data or the like obtained by X-ray imaging) from a data save device storing data existing in an intranet or the like and executes services on the Internet, in performing data processing of the target data, the data save device issues a new identifier (second identifier) different from the identifier (first identifier such as a check ID) attached to the target data, and deletes supplementary information that poses a problem when it is leaked. In addition, the data save device saves this new identifier together with the target data.

The data processing device performs data processing of the target data from the data save device, and returns the processed target data to the data save device. At this time, the data processing device attaches the new identifier to the target data when returning it to the data save device.

The data save device receives and saves the processed data from the data processing device. At the same time, on the basis of the new identifier attached to the processed data, the data save device searches for the original data (data before processing) of the processed data, and deletes the identifier (new identifier) which is stored in association with the searched data. This makes it possible to erase the association with the data.

In addition, the data save device issues a new identifier (third identifier) by using the new identifier issued at the time of data transmission to the data processing device and the current Greenwich time according to a specific algorithm, attaches it to the target data, and transmits the resultant data to the data processing device.

The data processing device determines whether the new identifier attached to the target data from the data save device is the identifier issued in a time zone with a specific time width before and after the current Greenwich time. This can prevent unspecified facilities from using services on the Internet.

The arrangement and operation of the data save processing system 106 according to the first embodiment will be described in detail below.

<Arrangement of Data Save Processing System 100>

As shown in FIG. 1, the data save processing system 100 is designed such that the data save device 200 which manages and saves data such as medical information on the hospital side and the data processing device 300 which processes the data can communicate with each other through a communication line.

The data save device 200 is, for example, a device on an intranet in a hospital, and the data processing device 300 is a device on the Internet.

Note that the communication line is typically one of the Internet, a LAN, a WAN, a telephone line, a dedicated digital line, an ATM, a frame relay line, a communication satellite line, a cable TV line, a data broadcast radio line, and the like or a so-called communication network realized by a combination of thereof and may have any arrangement as long as it allows data transmission/reception.

An image generating device 201 and image reference device 202 are connected to the data save device 200. The data save device 200 includes a generated data reception unit 211, data management unit 212, first changing unit 213, transfer unit 214, reception unit 215, save unit 216, second changing unit 217, reference device transmission unit 218, first identifier generating unit 219, change recording unit 220, second identifier generating unit 221, third identifier generating unit 222, and Greenwich time acquisition unit 223.

The data processing device 300 includes an authentication unit 301, processed data transfer unit 302, data processing unit 303, and Greenwich time acquisition unit 304.

The main functions of the data save device 200 and data processing device 300 will be described below.

In the data save device 200, the first identifier generating unit 219 generates the first identifier (check ID or the like) for identifying data (transfer data such as medical information) to be transferred to the data processing device 300 side (Internet side). The first identifier becomes part of the supplementary information of the corresponding transfer data.

The second identifier generating unit 221 generates the second identifier different from the first identifier generated by the first identifier generating unit 219.

The change recording unit 220 stores (records) the second identifier generated, by the second identifier generating unit 221, as supplementary information of the transfer data saved in the data management unit 212.

When the change recording unit 220 records the information, the first changing unit 213 simultaneously deletes the first identifier from the supplementary information of the transfer data and generates transfer data (identifier-changed data) to which the second identifier is attached.

The transfer unit 214 transfers the transfer data (identifier-changed data) obtained by the first changing unit 213 to the data processing device 300 side (Internet side).

The reception unit 215 receives processed data from the data processing device 300.

The save unit 216 saves the data received by the reception unit 215 in the data management unit 212.

The third identifier generating unit 222 generates the third identifier based on the second identifier according to a specific algorithm.

The first changing unit 213 attaches the third identifier generated by the third identifier generating unit 222 to the supplementary information of the transfer data, and transfers the resultant data to the data processing device 300 through the transfer unit 214.

In the data processing device 300, the authentication unit 301 receives the data transferred from the data save device 200 and compares the third identifier with the fourth identifier generated based on the second identifier of the received data according to the above algorithm in the data save device 200, thereby determining whether the fourth identifier coincides with the third identifier.

<Operation of Data Save Processing System 100>

First of all, on the data save device 200 side (intranet side), the external image generating device 201 outputs image data obtained by X-ray imaging.

The generated data reception unit 211 receives the image data output from the image generating device 201. This image data is, for example, an image obtained by X-ray imaging, to which attribute information including information (patient information) about the patient subjected to the X-ray imaging, examination information, and the like is attached as supplementary information.

When the generated data reception unit 211 receives image data, the first identifier generating unit 219 generates, for the image data, a unique identifier (first identifier) in the data management unit 212, and adds the identifier to the image data.

Note that, in addition to the above mode, the data save processing system 100 can use another mode of providing the first identifier depending on the facilities where the system is installed. This mode can be used on the precondition that the supplementary information of an image includes a check ID, and the check ID can be reliably used as a unique identifier in the data management unit 212 in operational facilities. In this case, the first identifier generating unit 219 extracts this check ID from the supplementary information of the image and sets it as a unique identifier (first identifier). Obviously, according to the gist of the present invention, the case wherein a check ID is extracted and used as the first identifier in this manner can be regarded as equivalent to the case wherein a unique identifier (first identifier) is generated in the data management unit 212.

The data management unit 212 saves the image data to which the first identifier is attached by the first identifier generating unit 219.

In this case, the data save device 200 is, for example, a device installed in a hospital. When image data saved in the data management unit 212 in the above manner is to be transferred to the data processing device 300 on the Internet side, the data save device 200 issues a new identifier, and at the same time deletes supplementary information that will cause a problem when it is leaked. This makes it possible to prevent data leakage.

More specifically, first of all, data to be transferred to the data processing device 300 must be sequentially processed. For this reason, the data save device 200 sequentially processes the data as transfer targets in the data management unit 212, and sends out them to the data processing device 300.

For the image data (target image data) newly saved in the data management unit 212, the second identifier different from the first identifier attached to the image data must be issued. The second identifier generating unit 221 therefore issues the second identifier.

The change recording unit 220 records the second identifier, generated by the second identifier generating unit 221, as supplementary information of the target image data in the data management unit 212.

The first changing unit 213 reads out the target image data from the data management unit 212 and deletes the first identifier of the data. At the same time, the first changing unit 213 adds the second identifier to the data.

The first changing unit 213 also deletes, of the supplementary information of the target image data, information about the patient corresponding to the target image data and all information that specifies the data itself, and more specifically, patient information such as the patient name and patient ID, the examination date, the examination date and time, and the like.

In this case, the first changing unit 213 does not delete minimum necessary information required for image expression, e.g., the numbers of pixels corresponding to the width and height of the image.

In order to perform authentication for data processing, the third identifier generating unit 222 generates the third identifier on the basis of the Greenwich time (processing time information) obtained by the Greenwich time acquisition unit 223 and the second identifier obtained by the second identifier generating unit 221.

For example, the third identifier generating unit 222 converts the current time (Greenwich time) into an elapsed minute based on 2000 (year)-01 (month)-01 (day) according to a predetermined algorithm, and adds the conversion result to the second identifier, thus generating the third identifier. That is, the third identifier is expressed as third identifier=$Mi+ID$ where Mi is the elapsed minute, and ID is the second identifier.

If, therefore, for example, the current Greenwich time is converted into an elapsed minute of 54,321 min (Mi) based on 2000 (year)-01 (month)-01 (day), and the second identifier is 98765 (ID), the third identifier is given by

54321+98765=153086

The first changing unit 213 attaches, to the target image data, the third identifier obtained by the third identifier generating unit 222 in this manner as supplementary information.

The transfer unit 214 sends out the target image data whose supplementary information is changed by the first changing unit 213 to the data processing device 300.

In the data processing device 300, the data processing unit 303 performs data processing for the image data (target image data) transferred from the data save device 200, but returns the second identifier to the data save device 200 through the processed data transfer unit 302 without changing the second identifier which is attached to the processed data.

In order to save a history of data processing, the data processing unit 303 saves the corresponding history information, second identifier, and supplementary information.

At the time of reception of the target image data from the data save device 200, the authentication unit 301 discriminates whether the target image data is sent from an authentic request source (the data save device 200 side in this case).

More specifically, the authentication unit 301 executes discrimination processing (authentication processing) according to the algorithm used by the third identifier generating unit 222 of the data save device 200. At this time, the authentication unit 301 permits target image data that falls within two min before and after the Greenwich time in minutes obtained by the Greenwich time acquisition unit 304.

Since the algorithm used in this case is an algorithm for a result that monotonously increases with a change in minute, if the third identifier of the target image data is ($Mi-2+ID$) or more and ($Mi+2+ID$) or less then the authentication unit 301 regards the target image data as data from an authentic request source (the data save device 200 side in this case).

As described above, the authentication unit 301 is configured to have a time margin. This is because correct times are not always set in both the data save device 200 and the data processing device 300, and a transfer time includes a delay time.

Assume that the result obtained by converting the current time (Greenwich time) into an elapsed minute based on 2000 (year)-01 (month)-01 (day) is 54321, and an allowable width of ±2 min is set, and that the second identifier of the target image data is 98765. In this case, if the third identifier of the target image data is 54321−2+98765=153084 or more and 54321+2+98765=153088 or less then the target image data is authentic.

Upon recognizing by the above authentication processing that the target image data is not authentic, the authentication unit 301 notifies the data processing unit 303 of the corresponding information (error occurrence). As a consequence, the data processing unit 303 stops data processing.

Even if, therefore, the third party maliciously saves transmission/reception data flowing on a network and sends out the data to the data processing device 300 afterward, the data processing device 300 does not authenticate the data because of the difference in Greenwich time.

The target image data (processed data) that is recognized as authentic data by the authentication unit 301 and subjected to data processing in the data processing unit 303 is sent out from the processed data transfer unit 302 to the data save device 200.

In the data save device 200, the reception unit 215 receives the processed data from the data processing device 300.

The save unit 216 saves the processed data received by the reception unit 215 in the data management unit 212.

After the data is completely saved in the save unit 216, the second changing unit 217 searches the data management unit 212 for data on the basis of the second identifier of the processed data. That is, the second changing unit 217 searches the data management unit 212 for the unprocessed target image data corresponding to the processed data, and deletes the second identifier attached to the target image data.

At this time, the second changing unit 217 adds partial information to the unprocessed target image data. This information includes, for example, information about the patient corresponding to the target image data, and information that specifies the data itself, and more specifically, patient information such as the patient name and patient ID, the examination date, and the examination date and time.

Note that the identifiers attached to these image data and added data may be set in the header field of the image data or separately managed as a database.

It cannot therefore be discriminated by using the second identifier saved by the data processing device 300 whether the data corresponds to any of the data held by the data management unit 212 in the data save device 200.

Image data managed by the data management unit 212, e.g., image data subjected to data processing in the data processing device 300 in the above manner, is transmitted from the reference device transmission unit 218 to the image reference device 202.

The image reference device 202 displays the image data from the reference device transmission unit 218 for imaging diagnosis or the like.

The image reference device cannot obtain any information that indicates the execution of data processing in the data processing device 300 on the Internet side.

Obviously, the object of the present invention is realized even by supplying a storage medium storing software program codes for realizing the functions of the data save device 200 or data processing device 300 according to the first embodiment to a system or apparatus, and causing the computer (or a CPU or MPU) of the system or apparatus to read out and execute the program codes stored in the storage medium.

In this case, the program codes read out from the storage medium realize the functions of this embodiment by themselves, and the storage medium storing the program codes constitutes the present invention.

As a storage medium for supplying the program codes, a ROM, flexible disk, hard disk, optical disk, magnetooptical disk, CD-ROM, CD-R, magnetic tape, nonvolatile memory card, or the like can be used.

The functions of this embodiment are realized not only when the readout program codes are executed by the computer but also when the OS or the like running on the computer performs part or all of actual processing on the basis of the instructions of the program codes.

The functions of this embodiment are also realized when the program codes read out from the storage medium are written in the memory of a function expansion board inserted into the computer or a function expansion unit connected to the computer, and the CPU of the function expansion board or function expansion unit performs part or all of actual processing on the basis of the instructions of the program codes.

Figure 2:
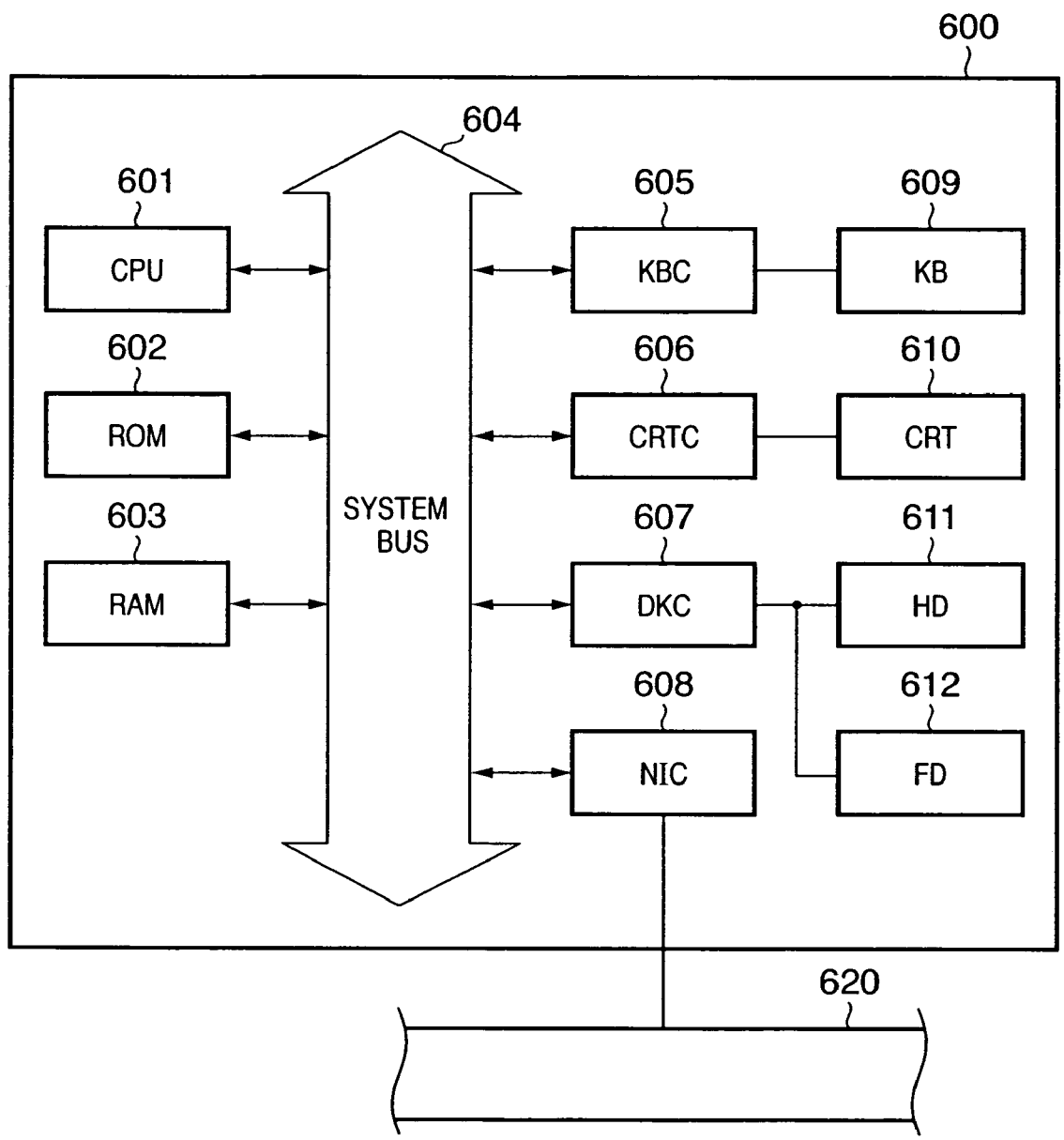
FIG. 2 is a block diagram showing the arrangement of a computer which reads out, from a computer-readable storage medium, a program for causing the computer to realize the function of the data save processing system according to the first embodiment of the present invention, and executes the program.

FIG. 2 shows a function 600 of the above computer (data save device 200 or data processing device 300).

As shown in FIG. 2, in the computer function 600, the following components are communicatively connected to each other through a system bus 604: a CPU 601, a ROM 602, RAM 603, a keyboard controller (KBC) 605 for a keyboard (KB) 609, a CRT controller (CRTC) 606 for a CRT display (CRT) 610 serving as a display unit, a disk controller (DKC) 607 for a hard disk (HD) 611 and a flexible disk (FD) 612, and a network interface controller (NIC) 608 for connection to a network 620.

The CPU 601 collectively controls the respective components connected to the system bus 604 by executing software stored in the ROM 602 or HD 611 or software supplied from the FD 612.

The CPU 601 performs control to realize the operation of this embodiment by reading out and executing a processing program based on a predetermined processing sequence from the ROM 602, HD 611, or FD 612.

The RAM 603 functions as a main memory, work area, or the like for the CPU 601.

The KBC 605 controls instruction input from the KB 609, a pointing device (not shown), or the like.

The CRTC 606 controls display on the CRT 610.

The DKC 607 controls access to the HD 611 and FD 612 which store a boot program, various applications, edit files, user files, a network management program, a predetermined processing program in this embodiment, and the like.

The NIC 608 bidirectionally exchanges data with an apparatus or system on the network 620.

As described above, according to the first embodiment, even if the data saving side (data save processing system 100) requests an external apparatus (data processing side (data processing device 300)) to process data, leakage of data from the data saving side can be prevented.

Although the ID (second identifier) managed by on the data saving side is identical to the ID (second identifier) of the information received on the data processing side, the ID (second identifier) managed on the data saving side is deleted at the timing when the data processing side returns the data processing result to the data saving side. Even if, therefore, data are stored on the data processing side, the data processing side cannot determine in the subsequent processing which data corresponds to which data on the data saving side. This makes it possible to prevent data leakage and data analysis.

Using the third identifier generated by a specific algorithm allows the data processing side to authenticate data. Even if, therefore, data transferred on a network is stolen and maliciously re-transmitted afterward, since the data processing side performs authentication based on the Greenwich time, erroneous authentication can be prevented.

Note that in the above data saving/processing system, the data processing device 300 may be made to function as a server, and the data save processing system 100 may be made to function as a client which uses the server.

The "server" in this case means, in WWW system, a Web server which stores information such as HTML documents and images and transmits information through a network such as the Internet upon reception of a request from client software such as a Web browser, or an application server (or a Web application server) which has a function of receiving a request from a user through a network and serving as a mediator for processing in the database system or the like.

In addition, the "client" means a computer and software which use the functions and data provided from a server in a network. For example, this client corresponds to a computer connected to a network, a home personal computer, and a Web browser, viewer, or the like which operates on a computer.

The first embodiment and the second to fourth embodiments to be described below can implement various kinds of processing associated with medical work between a client and a server under the Web environment through the Internet. However, the present invention is not limited to such an arrangement. The present invention can be applied to any arrangement as long as it is in a computer network environment which provides a form in which various operation windows for executing processes associated with the services provided by a server can be displayed on the browser (viewer) of a client.

SECOND EMBODIMENT

Conventionally, in making a diagnosis, one doctor generally examines one patient. In many cases, a doctor often requires a second opinion from another doctor or refers the patient to another hospital and entrusts a diagnosis to another doctor depending on the type of disease or the condition of the patient.

When, for example, a diabetic patient visits a physician, it may be diagnosed that the patient may have diabetic retinopathy. In this case, the patient preferably takes a medical examination from an ophthalmologist. If, however, no ophthalmology department exits within the same hospital facilities, the physician refers the patient to an ophthalmologist. In this case, the physician must write a letter of introduction and generate an examination data sheet and the like. The physician needs also to communicate with the ophthalmologist to whom the patient is referred. This requires much time and effort. In addition, the patient must regularly visit the physician and ophthalmologist, respectively.

In order to solve this problem, some physicians use a nonmydriatic fundus camera or the like to take fundus photographs of patient's eyes, and mail a photographed film or the like to an ophthalmologist, thereby entrusting the ophthalmologist with a diagnosis of retinopathy based on image interpretation. In addition, as disclosed in Japanese Patent Laid Open No. 2001-273365 (prior art 1), a cooperative diagnosis method of entrusting another doctor with a diagnosis by using a computer terminal connected to a network is used.

In the above method of mailing films, however, it takes time and trouble to mail data. In addition, films and reports may be lost during mailing. Furthermore, images such as films, patient data, examination data, and the report made by the ophthalmologist must be managed together. It therefore requires much labor in terms of clerical work.

Using a network poses the problem that "a doctor on the requesting side can browse all the registered information, and hence information associated with patient's privacy, e.g., the name of the patient, date of birth, and address may leak." This in turn poses, for example, the problem that "a doctor cannot entrust another doctor with a diagnosis for the sake of security protection of information, and hence cannot select an optimal diagnosing doctor."

In consideration of the above problems, the second embodiment is wherein when a cooperate diagnosis is to be performed by using a network, privacy is ensured by assigning different IDs to the examination requesting side and the examining side and performing conversion between the two IDs.

Figure 3:
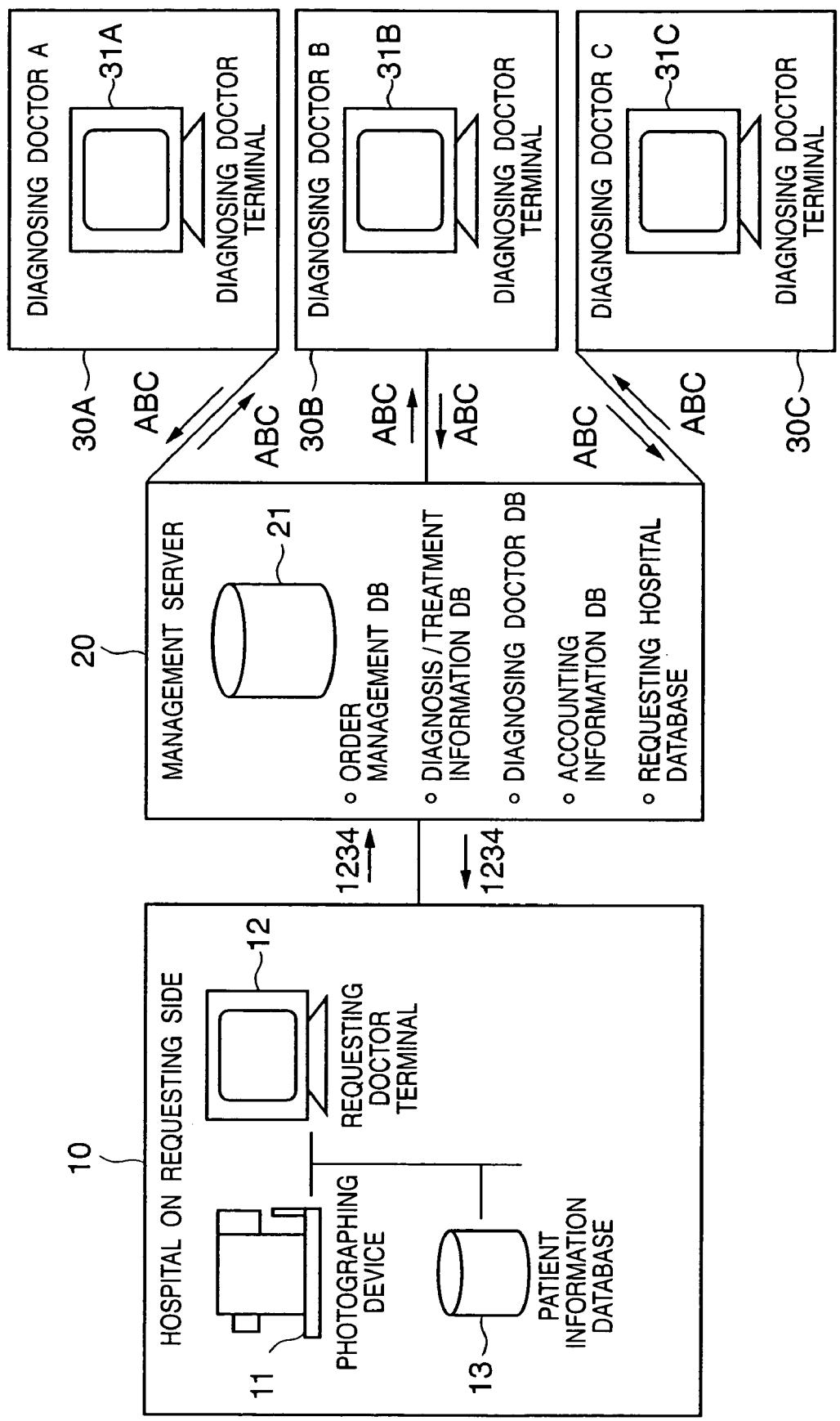
FIG. 3 is a view showing the arrangement of a system according to the second embodiment of the present invention.

FIG. 3 shows an example of the arrangement of a cooperative diagnosis system according to the second embodiment of the present invention.

Reference numeral 10 denotes a hospital on a requesting side, which includes a photographing apparatus 11 such as a fundus camera for photographing fundus images and a requesting doctor terminal 12 which records examination information, patient information, and the like together with photographed images to make a request to another doctor (diagnosing doctor).

Patient information registered at the time of reception of patients is stored in a patient information database (DB) 13. The patient information database 13 is connected to the photographing apparatus 11 and requesting doctor terminal 12. In photographing an image or requesting a diagnosis, therefore, patient information can be input by searching for patient information that has already been stored in a patient information database 13. The requesting doctor terminal 12 can connect to a management server 20 through a network such as a LAN or the Internet. The requesting doctor terminal 12 transmits processing target data such as a diagnosis request form to the management server 20 to register the data, thereby requesting another doctor to perform a diagnosis.

The management server 20 includes a diagnosis/treatment database storing various kinds of information associated with diagnoses, an order management database for managing diagnosis request orders, a diagnosing doctor database for managing registered doctor data, an accounting database for managing accounting to the requesting side/money distribution to the requested side, a requesting hospital database, and the like. The registered hospital 10 on the requesting side, various types of terminals of diagnosing doctors 30A, 30B, and 30C, and the like can connect to the management server 20 through a network. The management server 120 may be installed within the facilities of the hospital 10 on the requesting side or installed in facilities other than the hospital 10 on the requesting side which can be accessed through a public network such as the Internet.

The diagnosing doctors 30A, 30B, and 30C respectively have diagnosing doctor terminals 31A to 31C and can browse diagnosis requests imposed on themselves on their terminals, input diagnosis results, and register diagnosis result data by transmitting it to the management server 120 by accessing the management server 20 through a network.

A plurality of diagnosing doctors can share each of the diagnostic terminals 31A to 31C by making authentication using digital signatures, passwords, or the like. If an application used for a diagnosis is set as a Web-based application to allow execution of necessary processing such as request processing, browse processing, and diagnosis report processing by using a standard Web browser, a requested diagnosis can be processed from any kind of PC regardless of the type of terminal and OS, thus providing convenience.

Figure 4:
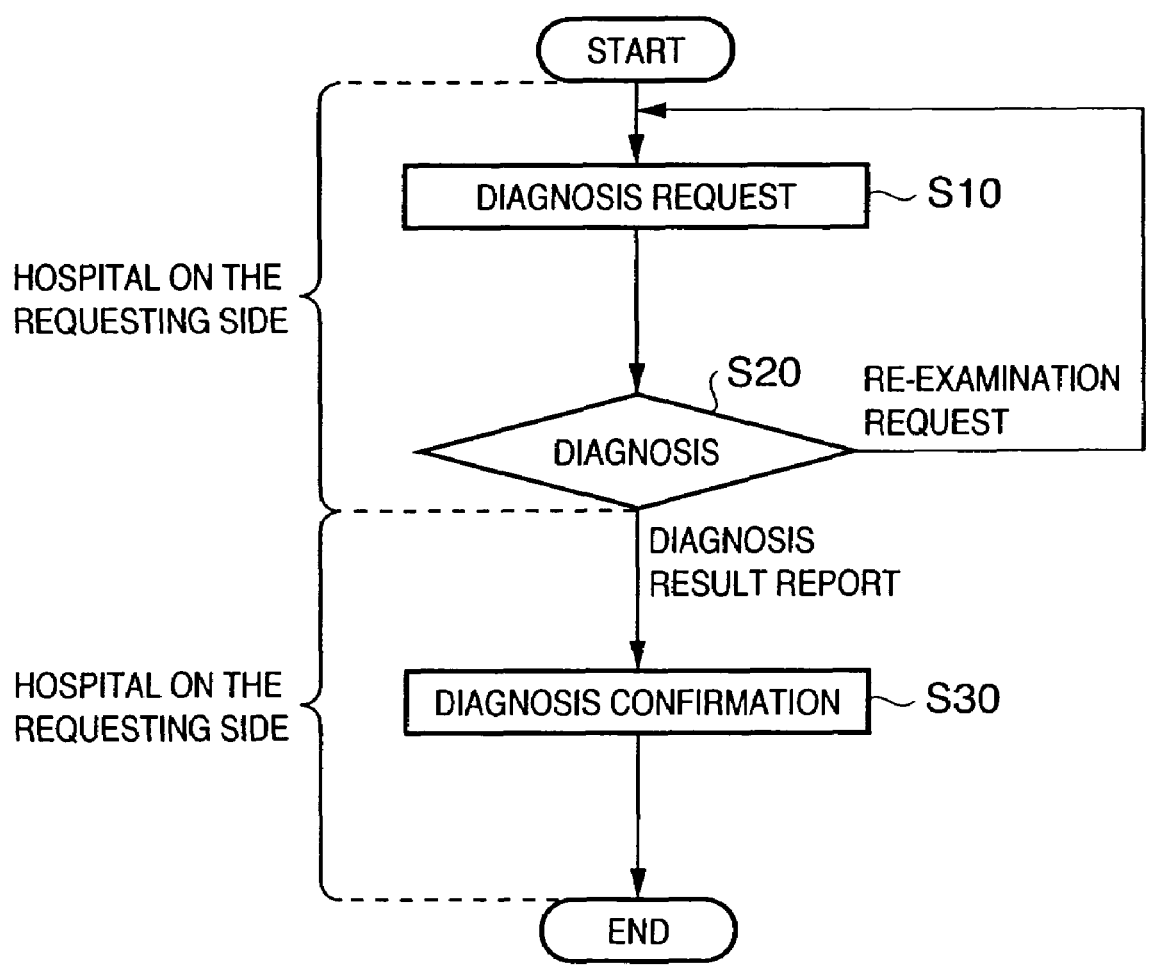
FIG. 4 is a flow chart for explaining the flow of a diagnosis request according to the second embodiment of the present invention.
Figure 5:
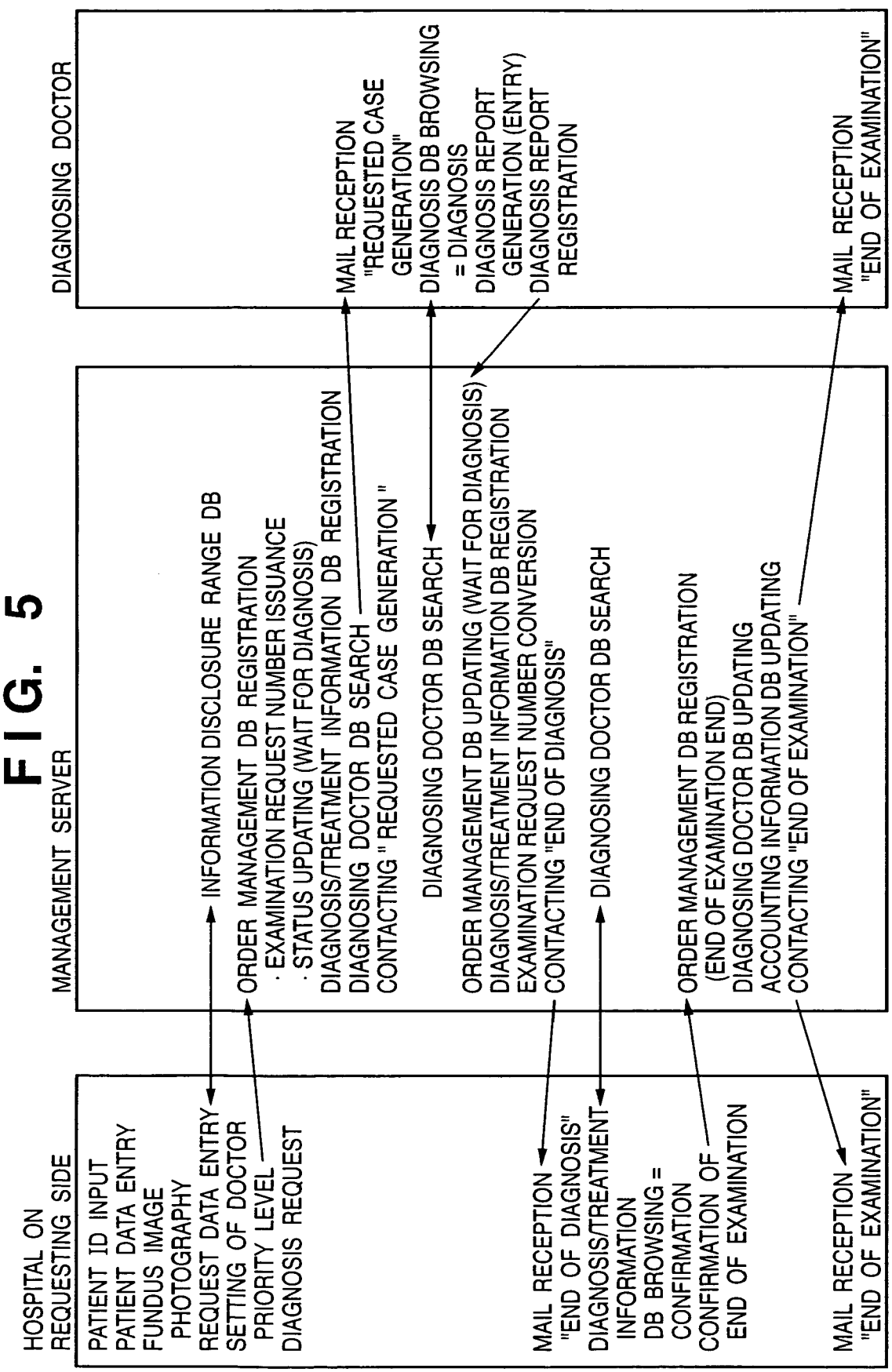
FIG. 5 is a view for explaining the flow of a diagnosis request job according to the second embodiment of the present invention.

A work flow in a case wherein a plurality of doctors cooperatively make a diagnosis by using this cooperative diagnosis system will be described next with reference to FIG. 4.

The hospital on the requesting side issues a diagnosis request to a diagnosing doctor A (diagnosing doctor terminal 31A) with the highest priority level through the management server 20 (S10). The diagnosing doctor A makes a diagnosis (S20) by image interpretation and transmits a diagnosis result report from the diagnosing doctor terminal 31A to the requesting doctor terminal 12 in the hospital 10 on the requesting side through the management server 20. The doctor on the requesting side confirms the received diagnosis result report by using the requesting doctor terminal 12 in the hospital 10 on the requesting side (S30). With this operation, this examination is finished.

Assume that when the diagnosing doctor A is requested to perform a diagnosis, he/she determines that he/she cannot make a diagnosis because the poor quality of diagnosis images, insufficient patient data, and the like. In this case, the doctor can issue a re-examination request from the diagnosing doctor terminal 31A to the requesting doctor terminal 12 in the hospital 10 on the requesting side through the management server 20. When a re-examination request is issued, the diagnosis request is canceled. The requesting doctor terminal 12 in the hospital on the requesting side is then notified of the corresponding information. With regard to the case for which the re-examination request has been issued, images are photographed again and patient data is added and corrected in the hospital 10 on the requesting side, and a diagnosis request is issued again as a new examination request.

The diagnosis request generated in the hospital 10 on the requesting side in this manner is finished when a diagnosis report is made or the request is canceled to issue a re-examination request. Assigning priority levels to diagnosing doctors in consideration of the schedules, specialties, and the like of the doctors in this manner can reliably make diagnosis requests.

If no diagnosis result report is made within a set deadline of a diagnosis result report, e.g., within one week after a diagnosis request, the management server 20 may automatically make a re-examination request and cancel the diagnosis request. This makes it possible to prevent the diagnosing doctor from stagnating in an examination.

A method of realizing the above work flow will be described in detail.

FIG. 3 shows the steps of processing to be performed by the requesting doctor terminal 12 in the hospital on the requesting side, a diagnosing doctor using a diagnosing doctor terminal, and the management server.

First of all, in the hospital 10 on the requesting side, an operator reads a patient's magnetic card with a magnetic card reader (not shown) connected to the photographing device 11, and inputs a patient ID. The operator then inputs data concerning the patient with a data input unit mounted on the photographing device 11. In this case, the patient data is constituted by personal information such as the name and address, diagnosis information such as sex, date of birth, weight, blood pressure, and medical history, and the like. The operator may retrieve these data from the patient information database 13 connected to the photographing device 11 through a network by using the patient ID as a key, and input the retrieved data.

Proper photographing conditions are then set for the photographing device 11 to photograph fundus images of the patient. The data of the fundus images photographed by the photographing device 11 are sent to the requesting doctor terminal 12 to be displayed on a diagnosis request form window like the one shown in FIG. 6.

On this diagnosis request form, in addition to the image data sent from the photographing device 11, the following data are sent and displayed: the patient data input by the photographing device 11 and data concerning the image, e.g., the image number, photographing apparatus, photography date and time, and distinction between the left and right eyes. An examination number is automatically issued for each diagnosis request so as to avoid overlapping within the hospital.

The doctor on the requesting side inputs request data, e.g., examination date and time, the name of a hospital, a hospital code, the name of a doctor in charge, an examination purpose, and the dead line of a diagnosis report, by using the requesting doctor terminal 12. Each of patient data can be added/corrected, as needed. The doctor may input patient data by using the requesting doctor terminal 12 through this diagnosis request form window after image transfer instead of the photographing device 11.

When the doctor clicks a diagnosing doctor selection setting button in the diagnosis request form window (FIG. 6), a diagnosing doctor selection setting window with a diagnosing doctor list is displayed, as shown in FIG. 7. The diagnosing doctor list includes, for example, the priority levels, names, specialties, titles, and work schedules of diagnosing doctors. These pieces of information are managed in the diagnosing doctor database of the management server 20.

The hospital 10 on the requesting side can set the priority levels of diagnosing doctors in advance in the diagnosing doctor database of the management server 20. The priority levels of diagnosing doctors can be changed by using a priority level changing button in the diagnosing doctor selection setting window. For example, the priority levels can be changed in accordance with a patient case or in consideration of the schedules of displayed diagnosing doctors. A diagnosis doctor can be added to or deleted from the diagnosing doctor list by operating diagnosing doctor add and delete buttons.

As described above, a diagnosis request from the hospital 10 on the requesting side is given to a diagnosing doctor with the highest priority level. In issuing a diagnosis request, the management server 20 searches the diagnosing doctor database to check the schedule of the diagnosing doctor with the highest priority level. If the schedule is not open for a predetermined period of time or more, the management server 20 displays, on the requesting doctor terminal 12, a window for allowing the doctor to select whether to request another doctor with the next highest priority level. This window displays, for example, a message like "Doctor XX cannot make any diagnosis report until December 16. Do you still want to request doctor XX to make a diagnosis? Or do you switch to doctor ○○?" The requesting doctor in the hospital 10 on the requesting side determines a diagnosing doctor by selects one of the choices in this window by using the requesting doctor terminal 12.

When an application button is clicked after the settings in the diagnosing doctor selection setting window (FIG. 7) are changed, the diagnosis request form window (FIG. 6) is restored, and at the same time, the changed settings are registered in the diagnosing doctor database of the management server 20. Subsequent diagnosis requests are processed in accordance with this condition. If no change is made in the setting associated with diagnosing doctors, this step can be omitted.

After changing the settings associated with the diagnosing doctors or changing the settings in a range, in the diagnosis request form window, which is released to public, the doctor on the requesting side returns to the diagnosis request form window (FIG. 6) to click a diagnosis request button upon checking input request data and the like. As a consequence, the contents of the diagnosis request form (diagnosis request form data) are transmitted to the management server 20. With this operation, the diagnosis request job is finished.

The transmitted diagnosis request form data is stored in the diagnosis information database after it is confirmed in the management server 20 that there is no defect concerning data items in the contents. In registering the data, a hospital code which is a number indicating the facilities of the hospital 10 on the requesting side is added to the examination number issued by the hospital 10 on the requesting side to generate a unique number on the management server 20. After it is confirmed that this number is not identical to any of the examination numbers that have already been registered, a new unique number is issued as an examination request number.

The management server 20 further registers the examination number of this examination and the examination request number in the order management database in association with each other. At the same time, data such as the occurrence date and time of the diagnosis request and the current status (wait for diagnosis) are recorded.

The management server 20 retrieves a diagnosing doctor with the highest priority level set in the diagnosing doctor selection list in association with this examination from the diagnosing doctor database. The management server 20 makes contact with the retrieved diagnosing doctor (e.g.., the diagnosing doctor A) by means such as e-mail transmission, indicating that a diagnosis request has been issued. At the same time, the management server 20 changes the setting of access level with respect to the diagnosis/treatment database to "browsing/reporting permitted".

When the diagnosing doctor A is made to know the generation of the diagnosis request through the diagnosing doctor terminal 31A, he/she accesses the management server 20 through the diagnosing doctor terminal 31A. Upon authenticating the diagnosing doctor A by using the ID, password, electronic signature, and the like, the management server 20 displays a diagnosis request list window like the one shown in FIG. 8 on the diagnosing doctor terminal 31A. Note that authentication with a fingerprint, iris, or the like can make a strict check to prevent someone from browsing diagnosis/treatment data or making a diagnosis report by disguising himself/herself as the diagnosing doctor A.

Figure 9:
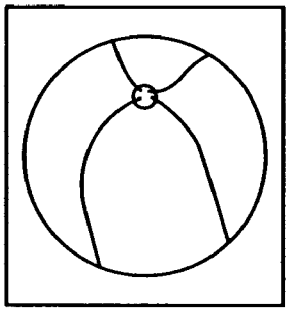
FIG. 9 is a view for explaining a diagnosis report window according to the second embodiment of the present invention.

When the diagnosing doctor A selects and displays one of the examination requests from the diagnosis request list through the terminal 31A, a diagnosis report window like the one shown in FIG. 9 is displayed. This diagnosis report window displays necessary data such as diagnosis request data, personal information of the patient, and image data, and allows the diagnosing doctor to input the result obtained by interpreting/diagnosing these displayed data in an diagnosis result entry field through the diagnosing doctor terminal 31A.

In order to ensure patient's privacy, the hospital 10 on the requesting side limits the contents in the diagnosis report window displayed on the diagnosing doctor terminal 31A with respect to the diagnosing doctor A to only items necessary for a diagnosis. The diagnosing doctor A cannot therefore browse personal information such as the address and telephone number of the patient. As for an examination number, only the examination request number issued by the management server 20 is displayed, and no examination number in the hospital 10 on the requesting side is displayed with respect to the diagnosing doctor A. There is no chance of violation of privacy concerning personal information of the patient.

In this manner, the hospital 10 on the requesting side can ensure privacy concerning personal information of a patient while disclosing only information necessary for a diagnosis to a diagnosing doctor.

By using a re-examination request button or report register button displayed in this diagnosis report window, the diagnosing doctor A can select re-examination request processing or report registration processing through the diagnosing doctor terminal 31A.

Upon determining that the quality of an image as a diagnosis target displayed in the diagnosis report window is not sufficient for an image interpretation/diagnosis or there is some suspicion in patient data such as the blood pressure and blood glucose level, the diagnosing doctor A can cancel this diagnosis request and request the hospital 10 on the requesting side to perform re-photographing by clicking the re-examination request button.

When the diagnosing doctor A inputs the diagnosis result in the result entry field and clicks the report register button, the data of the diagnosis report is transmitted to the management server 20. With this operation, the step for the diagnosis report is completed.

A procedure by which the diagnosing doctor A registers diagnosis report data will be described next. The diagnosing doctor browses image data, patient data, and the like in a diagnosis report window like the one shown in FIG. 9, and makes a diagnosis based on these data. The diagnosing doctor then inputs the diagnosis result including the name of a disease, findings, and the like in the diagnosis result entry field. When the report register button is clicked, the input diagnosis result data is transmitted to the management server 20.

Upon determining the absence of defects in the transmitted diagnosis result data, the management server 20 registers the diagnosis result data in the diagnosis/treatment database, and changes the status on the order management database to "end of diagnosis/wait for confirmation". The management server 20 then notifies the requesting doctor terminal 12 in the hospital 10 on the requesting side by mail or the like that the diagnosis result has been reported. In this case, the examination request number is inversely converted into the original examination number used to make the diagnosis request.

Upon reception of the diagnosis report mail, the requesting doctor terminal 12 in the hospital 10 on the requesting side accesses the management server 20. As a consequence, a diagnosis report confirmation window like the one shown in FIG. 10 is displayed. When the doctor clicks the request source confirmation button upon confirming the contents of the diagnosis result, the corresponding information is transmitted to the management server 20. In this diagnosis report confirmation window, there is no need to inhibit the disclosure of information for security protection, and hence the examination number in the hospital 10 on the requesting side and personal information of the patient are displayed as in the case of the diagnosis request form window.

The diagnosis request number used by the diagnosing doctor is displayed in the diagnosis report confirmation window or the like on the requesting doctor terminal 12 side, together with the examination number, to specify the examination when it is necessary to make a direct contact with the diagnosing doctor by telephone or the like as in case of an emergency.

The management server 20 updates the examination status of the order management database to "end of examination", registers the diagnosis report record in the diagnosing doctor database, and registers accounting/money distribution data in the accounting database. Finally, the management server 20 transmits e-mail indicating the completion of all operations for this examination to the requesting doctor terminal 12 in the hospital on the requesting side and the diagnosing doctor terminal of the diagnosing doctor who has made the diagnosis. With this operation, the examination is terminated.

THIRD EMBODIMENT

Figure 11:
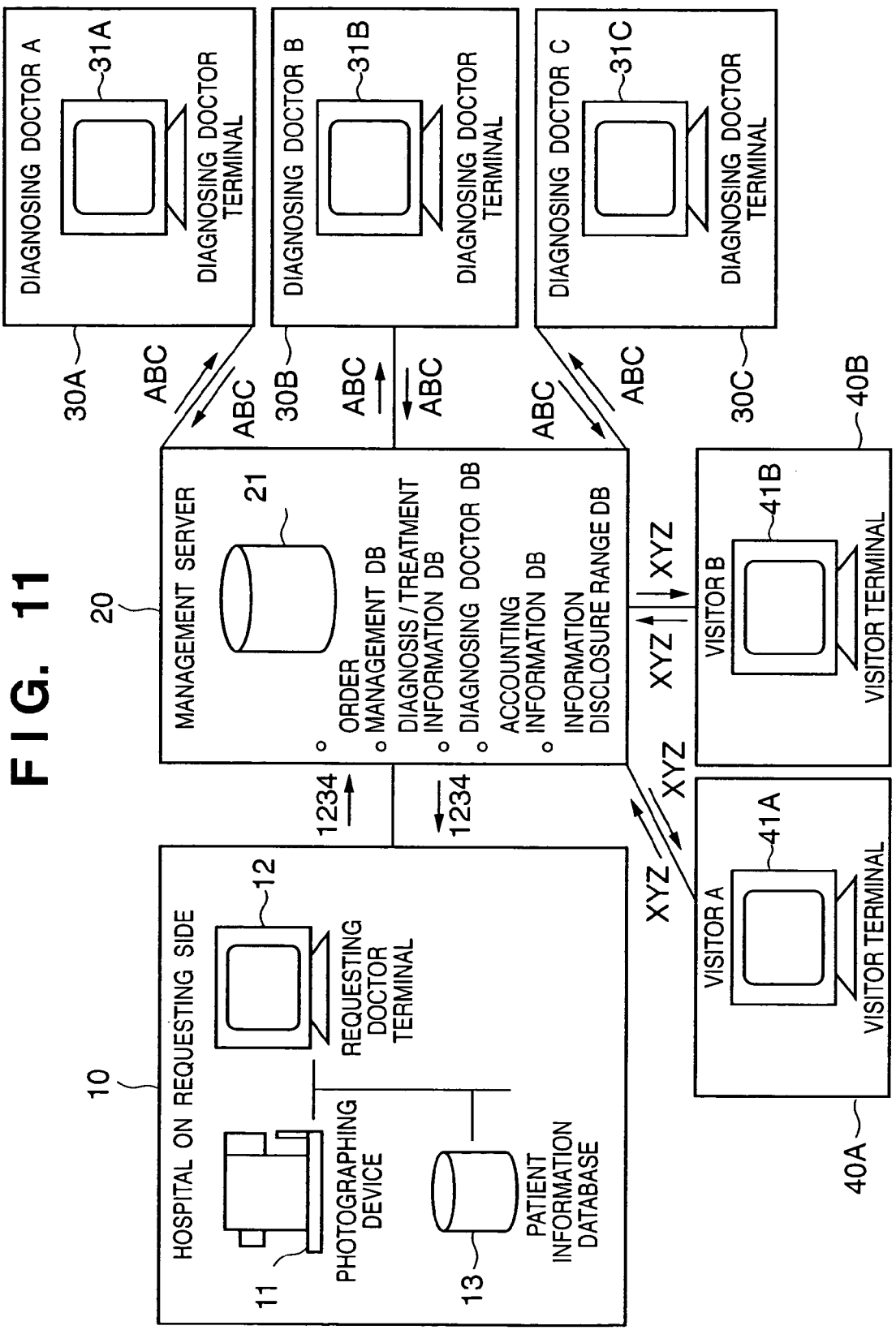
FIG. 11 is a view showing the arrangement of a system according to the third embodiment of the present invention.

As shown in FIG. 11, visitors A, B, and C (e.g., patients) other than diagnosing doctors may be allowed to access a management server 20 through visitor terminals 41A and 41B and browse diagnosis/treatment data concerning registered cases. In this case, the management server 20 may manage a browsing count, access time, or the like and charge a visitor in accordance with the amount of use.

In such a system, although a visitor can browse a diagnosis report and the like, the disclosure of personal information is inhibited, and an examination number is converted into a browsing ID number before it is displayed. This prevents the visitor from knowing the examination number, examination request number, and the like, and can present image data and diagnosis/treatment data such as a diagnosis result to the visitor while reliably ensuring security of personal information.

FOURTH EMBODIMENT

The fourth embodiment will be described next.

In the second embodiment, an examination is specified by using the examination number issued by the hospital 10 on the requesting side and the hospital code. If the unique number of an image which is used to make a diagnosis request, e.g., a DICOM image, is to be used, a study UID, which is a property of this image, can be used for the recognition of an examination at the time of registration. Since a study UID is always a unique value according to the DICOM specifications, this value can be used as a unique number on a management server 20 without being combined with a hospital code. Therefore, this number can be used after being converted into a unique examination request number on the management server.

According to the second to fourth embodiments, a plurality of doctors can efficiently and cooperatively make a diagnosis. A hospital on the requesting side, in particular, can make a diagnosis request to a doctor outside the hospital without disclosing any examination number used in the hospital to the doctor outside the hospital, thereby reliably ensuring security of private data such as personal information of a patient and a diagnosis result.

Each terminal and server described in each of the second to fourth embodiments is realized by the arrangement shown in FIG. 2.

In addition, the arrangement of the first embodiment can be applied to the cooperative diagnosis system according to the second to fourth embodiments. If, for example, the arrangement of the first embodiment is to be applied to the arrangement of the second embodiment, the function realized by the data save processing system 100 in FIG. 1 in the first embodiment is applied to the function realized by the requesting doctor terminal 12 and management server 20 in FIG. 2. The function realized by the data processing device 300 in FIG. 1 in the first embodiment is applied to each of the diagnosing doctor terminals 31A to 31C in FIG. 2 in the second embodiment. This makes it possible to realize a cooperative diagnosis while ensuring security of data in the first embodiment as well.

As many apparently widely different embodiments of the present invention can be made without departing from the spirit and scope thereof, it is to be understood that the invention is not limited to the specific embodiments thereof except as defined in the appended claims.

The invention claimed is:

1. An information processing apparatus which externally transfers target information to process the information, and saves the processed information, comprising:
   storage means for storing second identification information corresponding to the target information in association with the target information to which first identification information is attached;
   first changing means for deleting the first identification information and adding the corresponding second identification information to the target information in said storage means;
   transfer means for externally transferring the target information processed by said first changing means; and
   saving means for saving the target information processed at an external transfer destination to which the information is transferred by said transfer means; and second changing means for retrieving information from said storage means on the basis of the second identification information added to the target information processed at the external transfer destination and deleting the second identification information corresponding to the retrieved information from said storage means.

2. The information processing apparatus according to claim 1, further comprising second changing means for retrieving information from said storage means on the basis of the second identification information attached to the target information processed at the external transfer destination, and adding the information to the target information.

3. The information processing apparatus according to claim 1, wherein said first changing means deletes arbitrary information contained in the target information.

4. The information processing apparatus according to claim 1, wherein
   said first changing means adds third identification information generated by a predetermined algorithm based on the second identification information to the target information, and
   the third identification information contains information used for check processing at the external transfer destination to check whether the third identification information coincides with fourth identification information generated by the algorithm based on the second identification information of the target information.

5. The information processing apparatus according to claim 4, wherein
   the algorithm comprises an algorithm using the second identification information and processing time information, and
   the check processing comprises checking whether the third identification information coincides with a fourth identifier generated within a predetermined period of time before and after a processing time.

6. An information processing system in which a data saving side is communicatively connected to a data processing side which processes data transferred from the data saving side, wherein
   the data saving side comprises
   storage means for storing second identification information corresponding to the target information in association with the target information to which first identification information is attached,
   first changing means for deleting the first identification information and adding the corresponding second identification information to the target information in said storage means,
   transfer means for externally transferring the target information processed by said first changing means, and
   saving means for saving the target information processed at an external transfer destination to which the information is transferred by said transfer means; and second changing means for retrieving information from said storage means on the basis of the second identification information added to the target information processed at the external transfer destination and deleting the second identification information corresponding to the retrieved information from said storage means.

7. An information processing method of externally transferring target information to process the information, and saving the processed information, comprising:
   a storage step of storing, in a storage medium, second identification information corresponding to the target information in association with the target information to which first identification information is attached;
   a changing step of deleting the first identification information and adding the corresponding second identification information to the target information stored in the storage medium in the storage step;
   a transfer step of externally transferring the target information processed in the changing step; and
   a saving step of saving the target information processed at an external transfer destination to which the information is transferred in the transfer step; and second changing step for retrieving information from said storage medium on the basis of the second identification information added to the target information processed at the external transfer destination and deleting the second identification information corresponding to the retrieved information from said storage medium.

8. An information processing method of transferring target data managed on a data saving side to a data processing side upon attaching an identifier to the data, and receiving and saving the data processed on the data processing side, wherein
   a processing step on the data saving side comprises
   a first identifier attaching step of generating, as supplementary information, a first identifier for identifying the target data to be transferred to the data processing side, and attaching the supplementary information to the target data,
   a second identifier generating step of generating a second identifier different from the first identifier,
   a change storage step of storing the second identifier as supplementary information of the target data in a storage medium,
   a first changing step of deleting the first identifier from the supplementary information of the target data concurrently with storage of the second identifier in the storage medium in the change storage step, and attaching the second identifier to the target data, a transfer step of transferring the target data processed in the first changing step to the data processing side, a reception step of receiving the target data after data processing by the data processing side, and a saving step of saving the target data received in the reception step.

9. The information processing method according to claim 8, wherein the processing step on the data saving side further comprises a second changing step of retrieving data from management data on the basis of the second identifier of the target data after the target data is saved in the saving step, and deleting the second identifier corresponding to the retrieved data from the information stored in the change storage step.

10. The information processing method according to claim 8, wherein the first changing step comprises a step of deleting the first identifier, including partial information of the supplementary information of the target data in deleting the first identifier.

11. The information processing method according to claim 8, wherein the processing step on the data saving side further comprises a third identifier generating step of generating a third identifier according to a specific algorithm using the second identifier, the first changing step comprises a step of attaching the third identifier obtained in the third identifier generating step as supplementary information to the target data, and the processing step on the data processing side comprises an authentication step of checking whether a fourth identifier generated according to the algorithm using the second identifier of the target data from the data saving side coincides with the third identifier.

12. The information processing method according to claim 11, wherein the specific algorithm comprises an algorithm using the second identifier and Greenwich time, and the authentication step comprises a step of checking whether the third identifier coincides with the fourth identifier generated within a predetermined period of time before and after the current Greenwich time.

13. A computer-readable medium embodying a computer program for causing a computer to function as an information processing apparatus which externally transfers target information to process the information, and saves the processed information, comprising:

storage means for storing second identification information corresponding to the target information in association with the target information to which first identification information is attached;

first changing means for deleting the first identification information and adding the corresponding second identification information to the target information in the storage means;

transfer means for externally transferring the target information processed by the first changing means; and saving means for saving the target information processed at an external transfer destination to which the information is transferred by the transfer means; and second changing means for retrieving information from said storage means on the basis of the second identification information added to the target information processed at the external transfer destination and deleting the second identification information corresponding to the retrieved information from said storage means.

14. A computer-readable medium embodying a computer program for causing a computer to execute information processing transferring target data managed on a data saving side to a data processing side upon attaching an identifier to the data, and receiving and saving the data processed on the data processing side, wherein a processing step on the data saving side comprises a first identifier attaching step of generating, as supplementary information, a first identifier for identifying the target data to be transferred to the data processing side, and attaching the supplementary information to the target data, a second identifier generating step of generating a second identifier different from the first identifier, a change storage step of storing the second identifier as supplementary information of the target data in a storage medium, a first changing step of deleting the first identifier from the supplementary information of the target data concurrently with storage of the second identifier in the storage medium in the change storage step, and attaching the second identifier to the target data, a transfer step of transferring the target data processed in the first changing step to the data processing side, a reception step of receiving the target data after data processing by the data processing side, and a saving step of saving the target data received in the reception step.

15. An information processing apparatus which is connected, through a network, to a requesting terminal which generates diagnosis request data and a diagnosing terminal which input diagnosis result data with respect to the diagnosis request data, comprising:

first reception means for receiving, through the network, diagnosis request data to which a specific examination number is attached from the requesting terminal;

conversion means for converting the examination number attached to the diagnosis request data into an examination request number;

first transmission means for transmitting, to the diagnosing terminal through the network, the diagnosis request data to which the examination request number is attached;

second reception means for receiving the diagnosis result data with respect to the diagnosis request data from the diagnosing terminal through the network; and second transmission means for inversely converting the examination request number attached to the diagnosis result data into the examination number and transmitting the diagnosis result data to the requesting terminal through the network.

16. The information processing apparatus according to claim 15, wherein the examination number comprises a patient ID for specifying a patient.

17. The information processing apparatus according to claim 15, wherein said conversion means converts the examination number into the examination request number on the basis of a facility number representing a facility to which the requesting terminal belongs and the examination number.

18. The information processing apparatus according to claim 15, wherein said conversion means converts the examination number into the examination request number on the basis of a unique number of an image contained in the examination request data and the examination number.

19. An information processing system formed by mutually connecting, through a network, a requesting terminal which generates diagnosis request data, a diagnosing terminal which receives diagnosis result data with respect to the diagnosis request data, and a management server which performs transmission/reception of data and data management between the requesting terminal and the diagnosing terminal, wherein the requesting terminal comprises generating means for generating the diagnosis request data and attaching an examination number for specifying the diagnosis request data, first transmission means for transmitting the diagnosis request data to the management server through the network, and first reception means for receiving the diagnosis result data with respect to the diagnosis request data through the network, the management server comprises second reception means for receiving the diagnosis request data from the requesting terminal through the network, conversion means for converting the examination number attached to the diagnosis request data into an examination request number, second transmission means for transmitting, to the diagnosing terminal through the network, the diagnosis request data to which the examination request number is attached, third reception means for receiving the diagnosis result data with respect to the diagnosis request data from the diagnosing terminal through the network, and third transmission means for inversely converting the examination request number attached to the diagnosis result data into the examination number, and transmitting the diagnosis result data to the requesting terminal through the network, and the diagnosing terminal comprises fourth reception means for receiving, from the management server through the network, the diagnosis request data to which the examination request number is attached, input means for inputting diagnosis result data with respect to the diagnosis request data, and fourth transmission means for transmitting the diagnosis result data to the management server through the network.

20. An information processing method in an information processing apparatus connected, through a network, to a requesting terminal which generates diagnosis request data and a diagnosing terminal which inputs diagnosis result data with respect to the diagnosis request data, comprising:

a first reception step of receiving, from the requesting terminal through the network, diagnosis request data to which a specific examination number is attached;

a conversion step of converting the examination number attached to the diagnosis request data into an examination request number;

a first transmission step of transmitting, to the diagnosing terminal through the network, the diagnosis request data to which the examination request number is attached, a second reception step of receiving diagnosis result data with respect to the diagnosis request data from the diagnosing terminal through the network, and a second transmission step of inversely converting the examination request number attached to the diagnosis result data into the examination number, and transmitting the diagnosis result data to the requesting terminal through the network.

21. A computer-readable medium embodying a computer program for realizing information processing in an information processing apparatus connected, through a network, to a requesting terminal which generates diagnosis request data and a diagnosing terminal which inputs diagnosis result data with respect to the diagnosis request data, comprising:

a first reception step of receiving, from the requesting terminal through the network, diagnosis request data to which a specific examination number is attached;

a conversion step of converting the examination number attached to the diagnosis request data into an examination request number;

a first transmission step of transmitting, to the diagnosing terminal through the network, the diagnosis request data to which the examination request number is attached, a second reception step of receiving diagnosis result data with respect to the diagnosis request data from the diagnosing terminal through the network, and a second transmission step of inversely converting the examination request number attached to the diagnosis result data into the examination number, and transmitting the diagnosis result data to the requesting terminal through the network.

* * * * *